US011189373B2

(12) United States Patent
Schmidt et al.

(10) Patent No.: US 11,189,373 B2
(45) Date of Patent: Nov. 30, 2021

(54) INSTRUMENT AND METHOD FOR MONITORING AN ANALYTE CONCENTRATION

(71) Applicant: Roche Diabetes Care, Inc., Indianapolis, IN (US)

(72) Inventors: Wilfried Schmidt, Dannstadt-Schauernheim (DE); Bernd Steiger, Roemerberg (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 428 days.

(21) Appl. No.: 16/143,078

(22) Filed: Sep. 26, 2018

(65) Prior Publication Data
US 2019/0022314 A1 Jan. 24, 2019

Related U.S. Application Data

(63) Continuation of application No. PCT/EP2017/057487, filed on Mar. 30, 2017.

(30) Foreign Application Priority Data

Mar. 31, 2016 (EP) .................................... 16163425

(51) Int. Cl.
*G06F 3/0484* (2013.01)
*G16H 20/17* (2018.01)
(Continued)

(52) U.S. Cl.
CPC ......... *G16H 20/17* (2018.01); *A61B 5/14532* (2013.01); *A61M 5/1723* (2013.01);
(Continued)

(58) Field of Classification Search
CPC ........ A61M 2205/505; A61M 2205/52; A61M 2230/201; A61M 5/1723;
(Continued)

(56) References Cited

U.S. PATENT DOCUMENTS

2006/0137695 A1 6/2006 Hellwig et al.
2011/0201911 A1 8/2011 Johnson et al.
(Continued)

FOREIGN PATENT DOCUMENTS

CN 102902480 A 1/2013
CN 105308603 A 2/2016
(Continued)

OTHER PUBLICATIONS

International Search Report and Written Opinion of the International Searching Authority, PCT/EP2017/057487, dated Jun. 28, 2017, 10 pages.
(Continued)

*Primary Examiner* — Deanna K Hall
(74) *Attorney, Agent, or Firm* — Bose McKinney & Evans LLP

(57) ABSTRACT

A handheld display device for processing continuous sensor data has a communication interface, a graphical user interface having a gesture recognition component, a processor and a memory. The processor continuously receives time dependent sensor data, carbohydrate data, event data, and insulin data. The event data is indicative of a physical state of the subject. The processor determines a sensor data scaling factor, a carbohydrate data scaling factor and an insulin data scaling factor. The processor controls the graphical user interface to render a plot having single time, analyte concentration, carbohydrate amount, and insulin delivery amount axes. The analyte concentration axis is rendered on a first side of the plot and carbohydrate amount and insulin delivery amount axes are rendered on an opposite side of the plot, according to the scaling factors. The graphical user interface can be controlled with single and/or double finger gestures to magnify, shrink or shift axes.

15 Claims, 11 Drawing Sheets

(51) Int. Cl.
- *G16H 40/63* (2018.01)
- *G16H 40/67* (2018.01)
- *A61B 5/145* (2006.01)
- *A61M 5/172* (2006.01)
- *G06F 3/0488* (2013.01)
- *G16H 15/00* (2018.01)

(52) U.S. Cl.
CPC ...... *G06F 3/04845* (2013.01); *G06F 3/04883* (2013.01); *G16H 40/63* (2018.01); *G16H 40/67* (2018.01); *A61M 2205/3569* (2013.01); *A61M 2205/50* (2013.01); *A61M 2205/505* (2013.01); *A61M 2205/52* (2013.01); *A61M 2205/8206* (2013.01); *A61M 2230/201* (2013.01); *G06F 2203/04808* (2013.01); *G16H 15/00* (2018.01)

(58) Field of Classification Search
CPC ....... G06F 2203/04808; G06F 3/04845; G06F 3/04883; G16H 15/00; G16H 20/17; G16H 40/63; G16H 40/67
See application file for complete search history.

(56) References Cited

U.S. PATENT DOCUMENTS

| | | | |
|---|---|---|---|
| 2013/0067397 A1* | 3/2013 | Kirschner | G06F 3/04883 715/799 |
| 2014/0068487 A1* | 3/2014 | Steiger | G06F 19/00 715/771 |
| 2014/0094673 A1 | 4/2014 | Johnson et al. | |
| 2016/0097760 A1 | 4/2016 | Steiger et al. | |

FOREIGN PATENT DOCUMENTS

| | | |
|---|---|---|
| WO | WO 2006/066926 A1 | 6/2006 |
| WO | WO 2006/076930 A1 | 7/2006 |
| WO | WO 2013/097929 A1 | 7/2013 |
| WO | WO 2016/019192 A1 | 2/2016 |

OTHER PUBLICATIONS

International Preliminary on Patentability, PCT/EP2017/057487, dated Jun. 28, 2018, 25 pages.

Lodwig et al., Current Trends in Continuous Glucose Monitoring, Journal of Diabetes Science and Technology 8.2 (2014): 390-396.

* cited by examiner

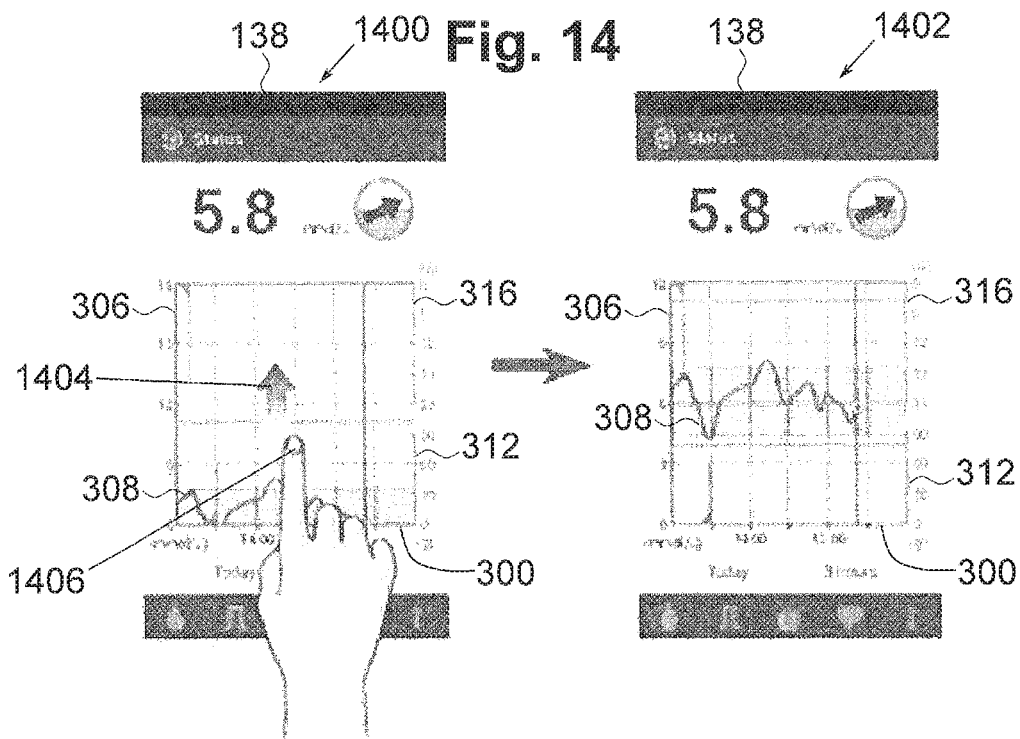
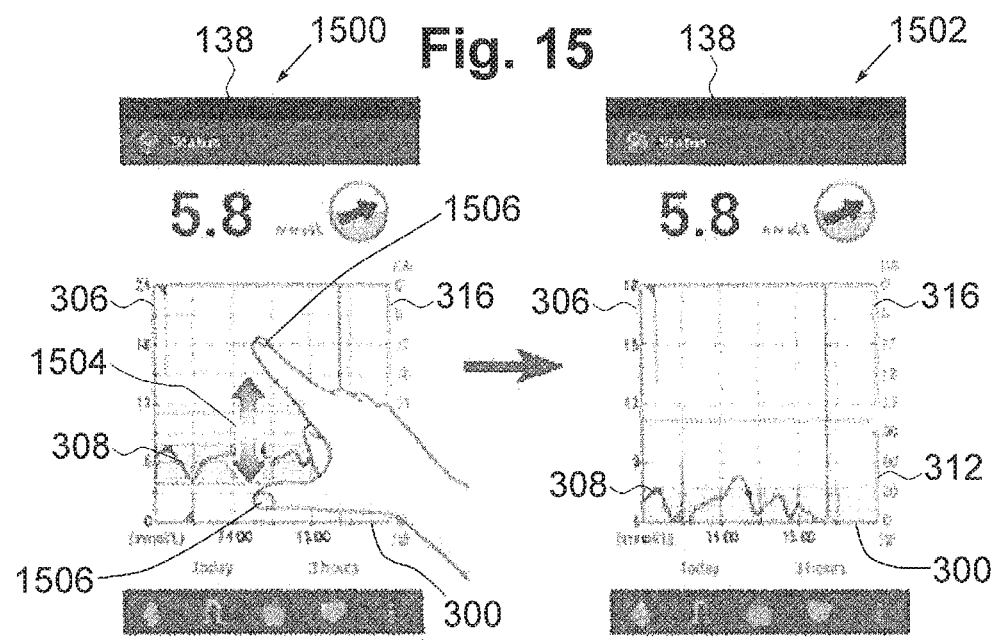

INSTRUMENT AND METHOD FOR MONITORING AN ANALYTE CONCENTRATION

RELATED APPLICATIONS

This application is a continuation of PCT/EP2017/057487, filed Mar. 30, 2017, which claims priority to EP 16 163 425.8, filed Mar. 31, 2016, both of which are hereby incorporated herein by reference in their entirety.

BACKGROUND

This disclosure relates to medical instrumentation, in particular instrumentation for analyte sensors for monitoring an analyte concentration of a subject.

The maintenance of certain chronic diseases may require a subject to accurately monitor an analyte level to maintain optimal health. For example, diabetics need to accurately monitor blood glucose levels to maintain proper health. The journal article Lodwig, Volker, et al. "Current trends in continuous glucose monitoring." Journal of diabetes science and technology 8.2 (2014): 390-396 discusses some current issues with glucose monitoring.

International patent application WO 2006/076930 discloses devices for sensing a concentration of chemical constituents in body fluid such as interstitial fluid, including but not limited to glucose. The devices and systems also measure and report the concentration of body fluid constituents at time intervals shorter than the physiological response time, thereby providing effectively continuous concentration measurements. The device has a probe, a reservoir with perfusion fluid connected to an inlet of the probe, at least one test zone which comprises a reagent to react with the analyte to produce a detectable change, a reader unit which reads test zones wetted with fluid containing the analyte, where the reader unit produces signals according to the concentration of the analyte in the fluid; and a processing unit for processing the signals and the concentration of the analyte.

United States Publication No. 2014/0094673 A1 discloses systems, methods and apparatus for processing, transmitting and displaying data received from an analyte sensor, such as a glucose sensor. The system may include a display device with at least one input device. In response to movement of or along the input device, the display device may change a glucose data output parameter and update an output of the display device using the changed output parameter.

SUMMARY

This disclosure teaches a handheld display device, a medical system, and a method of operating a handheld display device.

In one aspect this disclosure provides for a handheld display device for processing sensor data continuously measured by an analyte sensor. The analyte sensor is at least partially implantable. In some embodiments the analyte sensor may be implantable in a subcutaneous region. The handheld display device comprises a communication interface configured to receive sensor data from the analyte sensor via a communication channel. The communication channel is wired or wireless. The term sensor data as used here encompasses data which is descriptive of a measured analyte concentration. The sensor data may also be in a form of a raw sensor measurement, or it may be a calibrated analyte concentration. Conversion of the sensor data into a calibrated measurement can be performed by the handheld display device or by the body worn electronics making the measurement.

The handheld display device comprises a graphical user interface. This may for example be a touch or other display component which is used for displaying the graphical user interface. The handheld display device comprises a processor. The handheld display device further comprises a display device memory containing machine-executable instructions.

Execution of the machine-executable instructions causes the processor to continuously receive the sensor data via the communications interface. In this sense "continuously" receive may include in regular or irregular intervals the sensor data is either transmitted from a sensor part or requested by the handheld display device. The sensor data may be regularly or irregularly updated by the most recent measured sensor data. The sensor data is indicative or descriptive of an analyte concentration in a bodily fluid of a subject. The sensor data is time-dependent. In one example the body fluid may be an interstitial fluid.

Execution of the machine-executable instructions further causes the processor to receive carbohydrate data via the graphical user interface or via a carbohydrate data transfer interface. Receiving the carbohydrate data via the graphical user interface may for example involve a user inputting the type of foods or selecting foods from a library of foods. The user for example could select the foods on a graphical user interface and equivalent carbohydrate count via a program or mapping may then provide the carbohydrate data. Providing the carbohydrate data via the carbohydrate data transfer interface may for example comprise reading data by reading a code such as a QR code or an RFID tag attached to the food which may include a mapping or a carbohydrate value. In another example the carbohydrate data transfer interface may be a camera and the carbohydrate data may be received by taking a picture of the food and using image processing to make an estimate of the carbohydrates consumed.

Execution of the machine-executable instructions further causes the processor to receive event data via the graphical user interface or via an event data transfer interface. The event data is time-dependent. The event data is indicative or descriptive of a physical state or activity of the subject. Events like exercise or physical activity, stress or illness may be input by the user or provided by other application modules. For example calendar function including the event database may be stored within the handheld display device. In other examples the exercise, stress or illness data may be transferred from a wearable sensor with movement sensor and/or temperature sensor and/or a heart rate sensor. Such data events like stress, illness or exercise may be determined automatically or provided in conjunction with data input on the graphical user interface.

In some embodiments, the handheld or wearable device with the wearable sensor(s) may possibly determine the event data and this is simply transferred to the handheld display device. This may be done using a wired connection, an optical connection or wireless such as with a Bluetooth connection.

In another embodiment, the handheld display device itself may possibly comprise the wearable sensor(s).

In another embodiment, execution of the machine-executable instructions causes the processor to receive insulin data via the graphical user interface or via an insulin data transfer interface. In particular, insulin delivery may be simply input by a user on the graphical user interface or may be automatically transferred from other devices such as an insulin pen or an insulin pump. The insulin data transfer interface may for example be the same physical interface as the interface used to receive the sensor data. For example the data may be transferred via Bluetooth LE.

In another embodiment, execution of the machine-executable instructions further cause the processor to determine the sensor data scaling factor, a carbohydrate data scaling factor, and an insulin data scaling factor. The scaling factors, which are namely the sensor data scaling factor, the carbohydrate data scaling factor and the insulin data scaling factor, are based on an adjustable display timeframe and the corresponding data received in that adjustable display timeframe. The scaling factors may for example be fixed during a particular session or they may also be scaled continuously during the display of data on the graphical user interface. The adjustable display timeframe may for example either be pre-set or a user-selected timeframe. This may depend on adjusting the detection mechanism on the graphical user interface, for example a capacitive touch screen. The adjusted detection may include detecting capacitive changes and transferring them into a timeframe change. A typical zoom gesture on smart phones with at least two fingers would be an example for causing a capacitive change.

Execution of the machine-executable instructions further causes the processor to control the graphical user interface to render a plot on the graphical user interface. The plot comprises a single time axis and/or ordinate axis. The plot further comprises an analyte concentration axis, a carbohydrate amount axis, and an insulin delivery amount axis as an abscissa or abscissa axis. This may be considered to be the so called y-axis, where the single time axis may also be considered to be the so called x-axis. The plot then has a single x or time axis and the other quantities or axes are displayed perpendicular to the single time axis. Multiple amounts and types of data may therefore be plotted on the graphical user interface on a single plot. The analyte concentration axis is controlled to be rendered on a first side of the plot according to the sensor data scaling factor. The insulin delivery amount axis and the carbohydrate amount axis are controlled to be rendered on a second side opposite to the first side of the plot according to the insulin data scaling factor and the carbohydrate data scaling factor respectively. The analyte concentration axis, the carbohydrate amount axis and the insulin delivery amount axis may be perpendicular to the time axis. The sensor data is controlled to be rendered continually. The carbohydrate data is controlled to be rendered continually and/or as a carbohydrate discrete marker. A discrete marker may be an amount or icon or display plotted on the plot to convey the time and also possibly the amount of carbohydrate consumed. The insulin data is controlled to be rendered continually and/or as an insulin discrete marker. Likewise, the insulin discrete marker may be an object displayed on the plot which indicates when insulin was received and/or the amount of insulin. In the above, displaying continually refers to updating on a continual basis. The data for instance may be provided in discrete amounts via the communication channel. As the data may comprise different types, the display may be updated on a continual or rolling basis as data is received.

This embodiment may have the benefit that displaying all of the data on the single graph will allow a non-trained individual to more easily understand the interaction of the insulin and the analyte concentration as it interacts with the amount of carbohydrate and exercise or health condition.

The above embodiment may provide the benefit that the display of events and glucose level in one graph allow for a more simple overview of the metabolic state of the subject wearing the analyte sensor.

In another embodiment, the analyte concentration is a glucose concentration. The analyte sensor may be a subcutaneous glucose sensor.

In another embodiment, the sensor data and the corresponding display time scale are updated continuously. This may mean that they are updated on a rolling basis or as more data is received. The most recent sensor data point of the continually updated sensor is controlled to be rendered at a point in time. This may be earlier than the latest point in the time within the time axis.

In another embodiment, a prediction of future analyte values, based on the received sensor data, may be determined and controlled to be rendered continually on the graphical user interface.

In another embodiment, the rendered plot is scrollable on the time axis. The output of the warning is triggered if the current point in time is not displayed anymore.

In another embodiment, if the events are provided from other application modules, for example a calendar function including an event database, or a gesture on a touch screen, for example a tab of an event symbol on a plot, these may both open the event details from the event database or of the other application module.

In another embodiment, the graphical user interface may also be controlled to render historical sensor data. The historical sensor data may be the sensor data of e.g. one day in the past. The amount of historical data to be displayed may be dynamic in the sense that the number of days may be adjustable for the display.

In another embodiment, the medical system comprises a handheld display device according to an embodiment. The medical system further comprises a body worn portion configured for attaching to an outer surface of a subject. The body worn portion further comprises the analyte sensor. The body worn portion is configured for exchanging data with the handheld display device via a communication channel. This embodiment may be beneficial because it may provide an integrated system for using with the handheld display device and the analyte sensor.

In another embodiment, the analyte concentration is a glucose concentration. The sensor is a subcutaneous glucose sensor. This may be beneficial because it may provide for an effective means of managing the diabetes of the subject.

In another embodiment, execution of the machine-executable instructions further causes the processor to calculate a suggested bolus. The suggested bolus is calculated using at least one of a bolus model, the sensor data, the carbohydrate data, the insulin data, and the event data. The plot further comprises a bolus indicator. The bolus indicator displays an injection time and an injection amount. The injection amount is displayed on the time axis. The injection amount is displayed as a length perpendicular to the time axis. This embodiment may be beneficial because it may provide for an effective means of alerting a subject when and to what amount they should inject a bolus.

The suggested bolus may be calculated as is done in U.S. Publication No. 2006/0137695 A1. The entire disclosure of U.S. Publication No. 2006/0137695 A1 is incorporated by reference herein.

In another embodiment, the handheld display device is configured as a continuous glucose monitor that provides a continuous glucose measurement (CGM) using an analyte sensor providing the sensor data continuously or as a data stream.

In another embodiment, the suggested bolus is an augmented bolus recommendation. The augmented bolus is calculated based on the CGM measurement.

In another embodiment, the suggested bolus is a multi-wave bolus. The multi-wave bolus is a bolus which is suggested to be administered in two or more portions with a specified delay between each of the two or more portions.

In another embodiment, the suggested bolus is an amount of insulin to be delivered in order to adjust the blood glucose level reach or change to a predetermined or customized range. The amount of insulin may be a discrete amount of insulin. For example the range may be an euglycemic range. This embodiment may be beneficial because it may provide a means for a subject to self-manage their diabetes. For example the suggested bolus may be displayed before or after a meal to bring the blood glucose level within the predetermined or customized range.

In another embodiment, the medical system further comprises an event database. The event database is configured for logging any one of the following: the sensor data, the carbohydrate data, the event data, the insulin data, and combinations thereof. The inclusion of an event database may be beneficial because it may provide for a means of developing better models for predicting the proper bolus to be injected or for providing data which can be reviewed later by the subject or a medical professional.

In another embodiment, the medical system further comprises a learning algorithm module. The learning algorithm module is configured for correcting the bolus model using the event database. This may be beneficial because the bolus model can be adjusted for the individual subject using the handheld display device. The learning algorithm module may take different forms. For example a neural network, a principle components analysis module, or another module may be used to implement this.

In another embodiment, the body worn portion comprises the event database. This may be beneficial because it may provide for a means of providing for better security of the event database. If the event database is stored on the handheld display device it may be more easily compromised. For example the handheld display device may be a mobile telephone or tablet, which is widely available commercially and may therefore be susceptible to attack.

In another embodiment, the body worn portion comprises the learning algorithm module. This embodiment may also be beneficial because it provides the analysis of the long-term data away from the handheld display device, which, for the above mentioned reasons, may further improve the security of the event database and reduce the chances that it is stolen by a hacker or malicious code.

In another embodiment, the suggested bolus is displayed in response to received carbohydrate data. This embodiment may be beneficial because the subject may see the relationship of the carbohydrate data to the bolus. This may reduce the cognitive burden of the subject by displaying the direct relationship of the bolus to the carbohydrate.

In another embodiment, the received carbohydrate is an estimate of a meal or a predicted meal. This may for example be done by the input on a graphical user interface where the person selects the amount of carbohydrates consumed or selects amounts of food from a database. In other examples this may for example be done by receiving data such as RFID or barcode data which is then mapped onto carbohydrates. In another example it may also be that a picture is taken of the food using a camera on a handheld display device. This may then be used to pair the image to known images of food and make an estimate of the calories consumed.

In another embodiment, the medical system further comprises an insulin pump for injecting insulin at a basal rate and/or bolus into the subject. The plot further comprises a time-dependent display of the basal rate. This may be beneficial because it may provide for an integrated system for the management of diabetes. It may also be beneficial because it may provide for an effective way of monitoring the control function of the insulin pump relative to the various data collected about the subject.

In one embodiment, the basal rate is a continuous dosage intended to keep the glucose level in range under the assumption that no outside influences such as meal, sports or the like are present. Effectively the basal rate covers the insulin need in a steady state.

In another embodiment, the basal rate is a low, continuous dosage of 0.05 to 2 units of insulin per hour.

In another embodiment, the handheld medical device is a smartphone.

In another embodiment, execution of the machine-executable instructions further causes the processor to display a trend arrow. The direction of the trend arrow is dependent upon a current sensor data derivative value determined from the sensor data. For example the current value of the analyte from the sensor data may be determined and the derivative may be taken. This may be used to map onto a direction. This may provide visual feedback for the trend in the analyte value.

In another embodiment, execution of the machine-executable instructions further causes the processor to display a current glucose concentration value determined from the sensor date.

In another embodiment, execution of the machine-executable instructions may further cause the processor to display a current analyte value determined from the sensor data.

In another embodiment, the graphical user interface comprises a gesture recognition component. The gesture recognition component may for example be a touch screen.

In another embodiment, the graphical user interface is configured for receiving single finger gestures. The single finger gestures comprise a single finger motion parallel to a selected axis selected from the analyte concentration axis, the carbohydrate amount axis, and the insulin delivery amount axis. Execution of the machine executable instructions further cause the processor to shift the selected axis using the single finger motion.

In another embodiment, the graphical user interface is configured for receiving double finger gestures. The double finger gestures comprise a double finger motion parallel to a selected axis selected from the analyte concentration axis, the carbohydrate amount axis, and the insulin delivery amount axis. The double finger motion is descriptive of an increase or decrease of distance between two fingers measured along the selected axis. Execution of the machine executable instructions further cause the processor to magnify or shrink the selected axis using the increase or decrease of the distance between the two fingers measured along the selected axis.

In another aspect, this disclosure provides for a method of operating a handheld display device for processing sensor data continuously measured by an analyte sensor. The analyte sensor is at least partially implantable. The handheld display device comprises a communication interface configured to receive sensor data from the analyte sensor via a communications channel. The communication channel is wired or wireless. The handheld display device comprises a graphical user interface.

The method may comprise continuously receiving the sensor data from the communication interface. The sensor date is indicative of an analyte concentration in bodily fluid of a subject. The sensor data is time-dependent. The method further comprises receiving carbohydrate data via the graphical user interface or via a carbohydrate data transfer interface. The carbohydrate data is time-dependent. The carbohydrate data is indicative of carbohydrate intake by the subject.

The method further comprises receiving event data via the graphical user interface or via an event data transfer interface. The event data is time-dependent. The event data is indicative of the physical state of the subject. The method further comprises receiving insulin data via the graphical user interface or via an insulin data transfer interface. The insulin data is time-dependent. The insulin data is indicative of an insulin delivery to the subject. The method further comprises determining a sensor data scaling factor, a carbohydrate data scaling factor and an insulin data scaling factor. The scaling factors are based on an adjustable display timeframe and the corresponding data received in that adjustable display timeframe. The method further comprises controlling the graphical user interface to render a plot on the graphical user interface. The plot comprises a single time axis corresponding to a display timeframe as an ordinate or ordinate axis. The plot further comprises an analyte concentration axis, a carbohydrate amount axis, an insulin delivery amount axis as an abscissa or abscissa axis. The analyte concentration axis is controlled to be rendered on a first side of the plot according to the sensor data scaling factor. The analyte concentration axis and the carbohydrate amount axis are controlled to be rendered on a second side opposite to the first side of the plot according to the carbohydrate data scaling factor and the insulin data scaling factor respectively. The sensor data is controlled to be rendered continually. The carbohydrate data is controlled to be rendered continually and/or as a carbohydrate discrete marker. The insulin data is controlled to be rendered continually and/or as an insulin discrete marker.

In another embodiment, the graphical user comprises a gesture recognition component. The graphical user interface is configured for receiving single finger gestures. The single finger gestures comprise a single finger motion parallel to a selected axis selected from the analyte concentration axis, the carbohydrate amount axis, and the insulin delivery amount axis. The graphical user interface is configured for receiving double finger gestures. The double finger gestures comprise a double finger motion parallel to a selected axis selected from the analyte concentration axis, the carbohydrate amount axis, and the insulin delivery amount axis. The double finger motion is descriptive of an increase or decrease of distance between two fingers measured along the selected axis.

The method comprises receiving the double finger motion from the gesture recognition component, controlling the graphical user interface to magnify or shrink the selected axis using the increase or decrease of the distance between the two fingers measured along the selected axis, receiving the single finger motion from the gesture recognition component, and controlling the graphical user interface to shift the selected axis using the single finger motion.

In another aspect, this disclosure provides for a computer program product comprising machine-executable instructions for execution by a processor controlling the handheld display device for processing sensor data continuously measured by an analyte sensor. The analyte sensor is at least partially implantable. The handheld display device comprises an communication interface configured to receive sensor data from the analyte sensor via a communications channel. The communication channel may be, for example, wired or wireless.

The handheld display device comprises a graphical user interface. Execution of the machine-executable instructions causes the processor to continuously receive the sensor data via the communication interface. The sensor data is indicative of an analyte concentration of bodily fluid of a subject. The sensor data is time-dependent. Execution of the machine-executable instructions further causes the processor to receive carbohydrate data via the graphical user interface or via a carbohydrate data transfer interface. The carbohydrate data is time-dependent. The carbohydrate data is indicative of carbohydrate intake by the subject. Execution of the machine-executable instructions further causes the processor to receive event data via the graphical user interface or via an event data transfer interface. The event data is time-dependent. The event data is indicative of the physical state of the subject.

Execution of the machine-executable instructions further causes the processor to receive insulin data via the graphical user interface or via an insulin data transfer interface. The insulin data is time-dependent. The insulin data is indicative of an insulin delivery to the subject. Execution of the machine-executable instructions further causes the processor to determine a sensor data scaling factor, a carbohydrate data scaling factor and an insulin data scaling factor. The scaling factors are based on an adjustable display timeframe the corresponding data received in that adjustable display timeframe. The corresponding data here may refer to sensor data, carbohydrate data, and/or insulin data.

Execution of the machine-executable instructions further cause the processor to control the graphical user interface to render a plot on the graphical user interface. The plot comprises a single time axis corresponding to a display timeframe as an ordinate or ordinate axis. The plot further comprises an analyte concentration axis, a carbohydrate amount axis, and an insulin delivery amount axis as an abscissa. The analyte concentration axis is controlled to be rendered on a first side of the plot according to the sensor data scaling factor. The analyte concentration axis and the carbohydrate amount axis are controlled to be rendered on a second side opposite to the first side of the plot according to the carbohydrate data scaling factor and the insulin data scaling factor respectively. The sensor data is controlled to be rendered continually. The carbohydrate data is controlled to be rendered continually and/or as a carbohydrate discrete marker. The insulin data is controlled to be rendered continually and/or as an insulin discrete marker.

It is understood that one or more of the aforementioned embodiments may be combined as long as the combined embodiments are not mutually exclusive.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIG. 14 shows two views of a graphical user interface; and

FIG. 15 shows two additional views of a graphical user interface.

DESCRIPTION

The embodiments described below are not intended to be exhaustive or to limit the invention to the precise forms disclosed in the following description. Rather, the embodiments are chosen and described so that others skilled in the art may appreciate and understand the principles and practices of this disclosure.

Like numbered elements in these figures are either equivalent elements or perform the same function. Elements which have been discussed previously will not necessarily be discussed in later figures if the function is equivalent.

Figure 1:
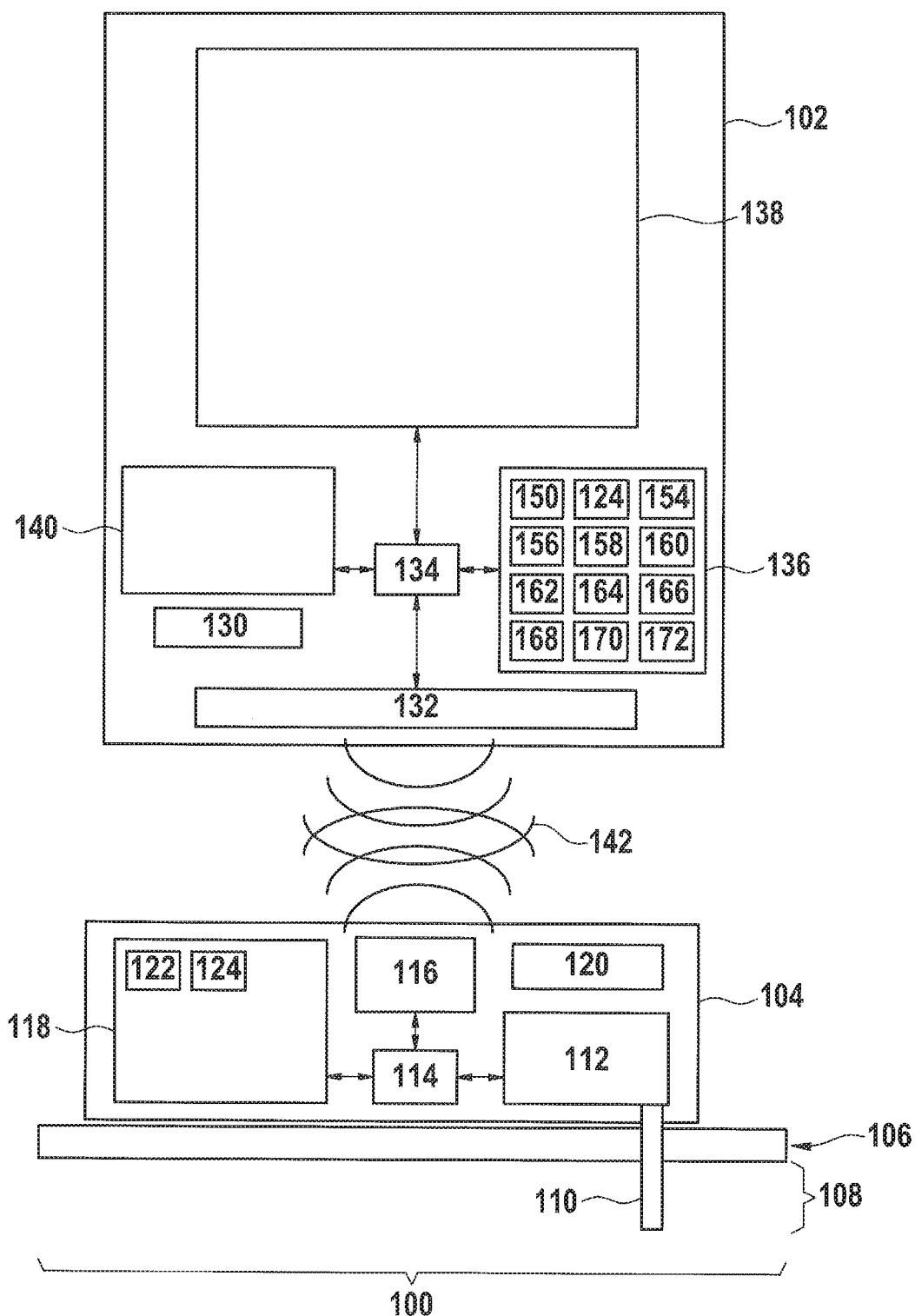
FIG. 1 illustrates an example of a medical system with a handheld display device.

FIG. 1 shows an example of a medical system 100. The medical system 100 comprises a handheld display device 102 and a body worn portion 104. In this example the body worn portion 104 is seen as being attached to the skin 106 of a subject. Below the skin is a subcutaneous region 108 of the subject. The body worn portion 104 has a subcutaneous portion 110 that extends through the skin 106 into the subcutaneous region 108. The subcutaneous portion 110 may represent one or more cannulas and/or it may represent one or more sensors, which are inserted into the subcutaneous region 108. The subcutaneous portion 110 is seen as being connected to a medical module 112.

The medical module may comprise one or more monitoring systems for recording data from the one or more sensors and the medical module 112 may also comprise one or more pumps with reservoirs for pumping fluid such as insulin or glucagon into the subcutaneous region 108 via one or more cannulas. The medical module 112 is seen as being controlled by a first processor 114. The first processor 114 is further shown as being connected to a first wireless communication module 116 and a first memory 118. The body worn portion 104 is powered by a first battery 120. The first memory 118 is shown as containing body worn portion instructions 122. The body worn portion instructions 122 comprise instructions which enable the first processor 114 to operate the body worn portion 104.

The body worn portion instructions 122 may for instance contain commands for controlling the medical module 112 and for getting the first wireless communication module 116 to communicate with the handheld display device 102. The first memory 118 is further shown as containing an analyte concentration 124 that was measured using a sensor that is part of the subcutaneous portion 110.

The handheld display device 102 is shown as comprising a second battery 130 which is used to power the handheld display device 102. The handheld display device 102 further comprises a communication interface which is also referred to herein as the second wireless communication module 132. The second wireless communication module 132 is shown as being connected to a second processor 134. The second processor may also be referred to as the processor. The label "second processor" is used to distinguish it from the first processor 114 of the body worn portion 104. The second processor is also connected to a second memory 136 and a data exchange interface 150. The data exchange interface 150 may be used to communicate with other communication networks or computers or controllers. The data exchange interface 150 may be optional in some examples. In some examples, the data exchange interface is used to communicate with digital mobile telephone networks.

The handheld display device 102 is further shown as containing a display 138 with a graphical user interface. The display 138 may for example be touch screen or a capacitive touch screen. The details of the graphical user interface are detailed in later Figures. The second memory is shown as containing an operating system 150 for the handheld display device 102. The second memory 136 is further shown as containing the analyte concentration 124 that has been transferred via the communication channel 142. The second memory 136 is further shown as containing carbohydrate data 154, insulin data 156, and event data 158. This data 154, 156, 158 may have been input manually using the graphical user interface 138 or may have been received via other sensors or by other means such as the data exchange interface 140. The second memory 136 is further shown as containing sensor data scaling factor 160, the carbohydrate data scaling factor 162 and an insulin data scaling factor 164 that are used in the generation of the plot on the graphical user interface 138.

The second memory 136 is further shown as containing executable instructions 166 which are used to control the method or operations of displaying the plot and collecting the data for displaying the plot. The second memory 136 is further shown as containing an event database 168 where the insulin data 156, the event data 158 and/or the carbohydrate data 154 are logged and stored. The second memory 136 is further shown as containing learning algorithm instructions 170 and bolus model instructions 172. The bolus model instructions 172 may be used for generating a recommended or desired bolus. The learning algorithm instructions 170 may use the event database 168 to correct or improve the bolus model instructions so that a more accurate bolus is calculated.

Figure 2:
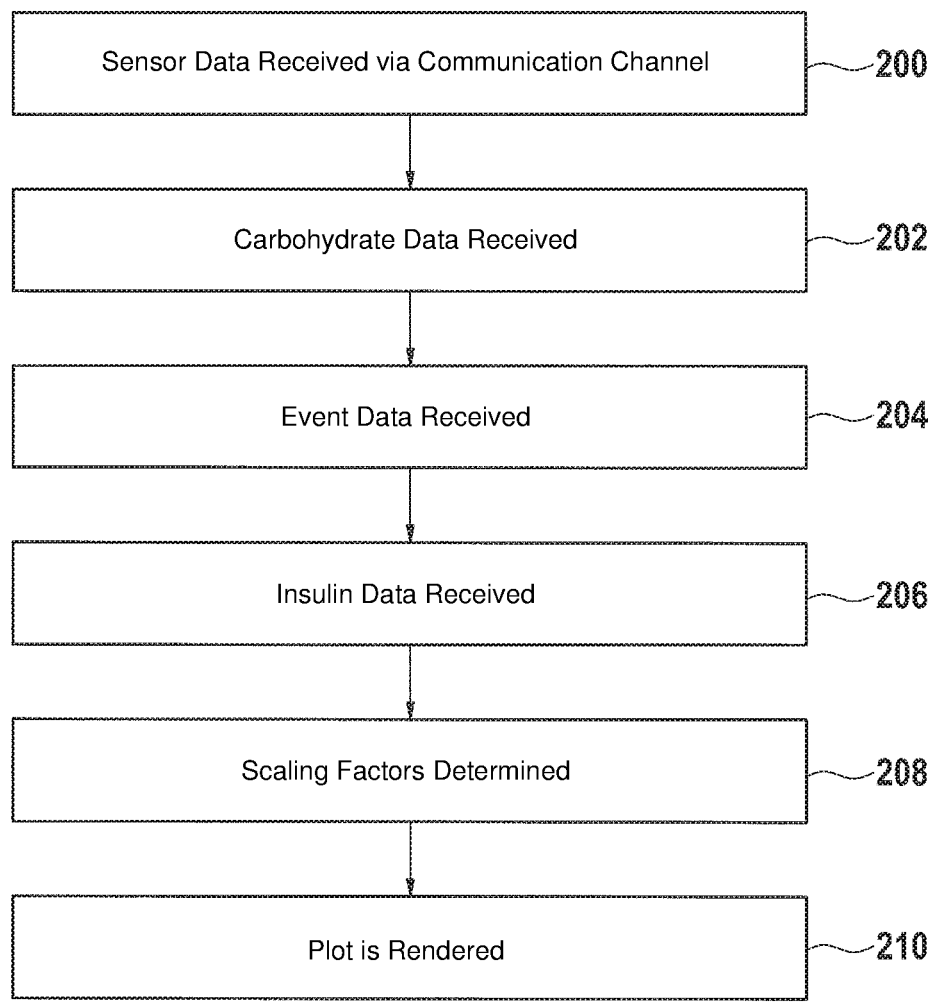
FIG. 2 shows a flow chart which illustrates an example of how to use the medical system of claim 1.

FIG. 2 shows a flowchart, which illustrates a method of operating the medical system 100 of FIG. 1. The method as described in FIG. 2 may also be used to apply to the operation of only the handheld display device 102. First in step 200 sensor data 124 is received via the communication channel 142. The sensor data 124 is indicative of an analyte concentration in bodily fluid of a subject. The sensor data is time-dependent. Next in step 202 carbohydrate data 154 is received via the graphical user interface 138 or via a carbohydrate data transfer interface. The carbohydrate data is time-dependent. The carbohydrate data is indicative of carbohydrate intake by the subject. In step 204 the event data 158 is received via the graphical user interface 138 or via an event data transfer interface. The event data is time-dependent. The event data is indicative of the physical state of the subject. Next in step 206 insulin data 164 is received via the graphical user interface 138 or via an insulin data transfer interface. The insulin data is time-dependent. The insulin data is indicative of an insulin delivery to the subject. Next in step 208 a sensor data scaling factor 160, a carbohydrate data scaling factor 162 and an insulin data scaling factor 164 are determined.

The scaling factors are based on an adjustable display timeframe and the corresponding data received in that adjustable display timeframe. Finally, in step 210 the second processor controls the graphical user interface 138 to render a plot on the graphical user interface. The plot also displays an analyte concentration axis, a carbohydrate amount axis, and an insulin delivery amount axis. The analyte concentration axis is controlled to be rendered on a first side of the plot according to the sensor data scaling factor. The analyte concentration axis and the carbohydrate amount axis are controlled to be rendered on a second side opposite to the first side of the plot according to the carbohydrate data scaling factor and the insulin data scaling factor. The sensor data is controlled to be rendered continually. The carbohydrate data is controlled to be rendered continually and/or as a carbohydrate discrete marker. The insulin data is controlled to be rendered continually and/or as an insulin discrete marker.

Figure 3:
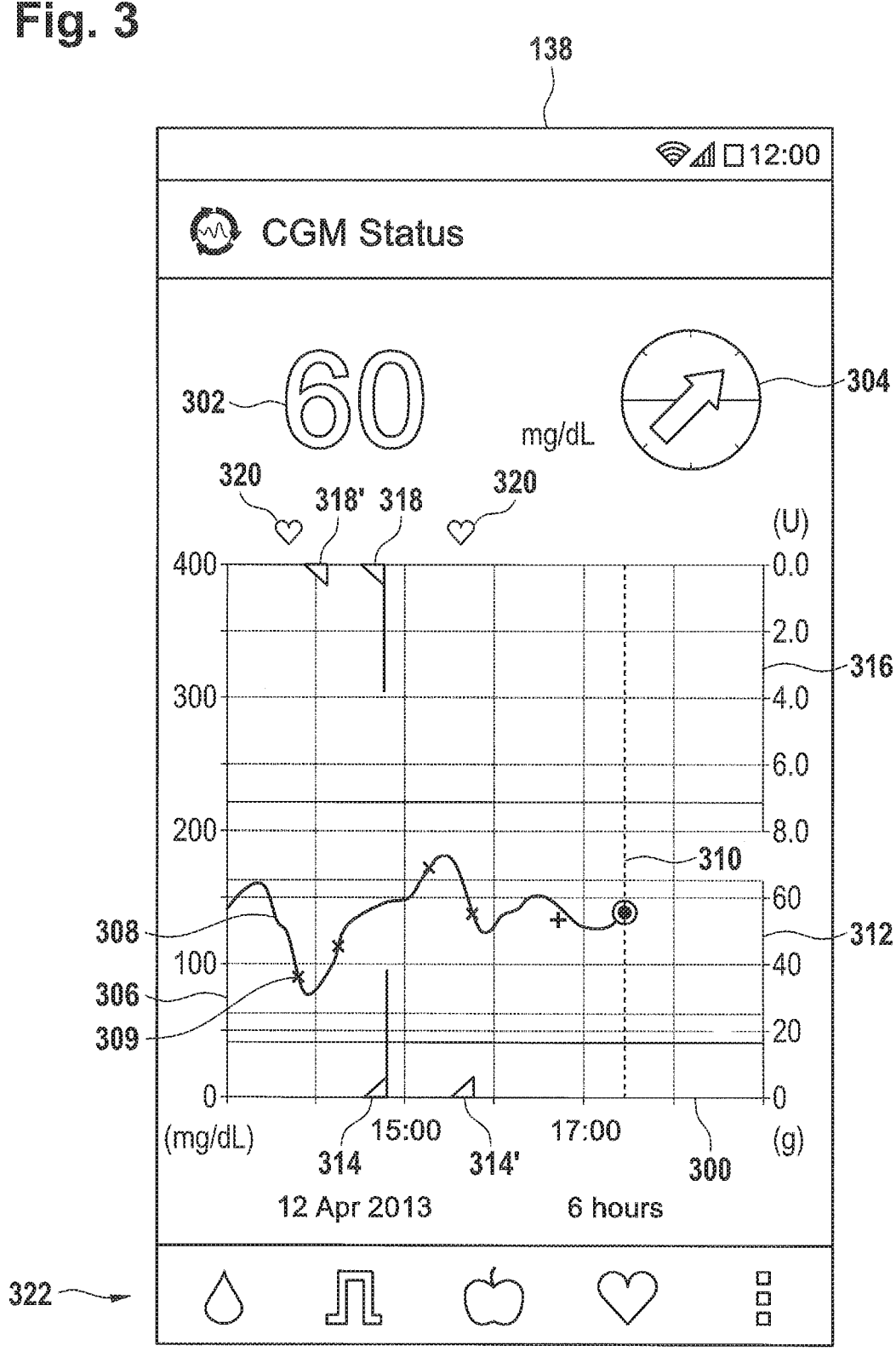
FIG. 3 illustrates an example of a graphical user interface.

FIG. 3 shows an example of the user interface 138. The user interface displays a plot as a single time axis 300. The single time axis 300 may be considered to be an adjustable display time frame. The graphical user interface also displays a current sensor data value 302. This may be an analyte concentration. Next to this is a trend arrow 304 which shows the trend of the current sensor data value 302. The plot also has an analyte concentration axis 306. Using this axis 306 there is a plot of the analyte concentration 308. In this case the axis indicates blood measurements 309 which are used to calibrate the plot of the analyte concentration 308. The cursor 310 shows the current time on the plot. In some examples the user may be able to manipulate the current time sensor 310 and the values 302 and the trend arrow 304 may adjust according to the chosen time 300. The plot further has a carbohydrate amount axis 312. Corresponding to this axis are carbohydrate discrete markers 314 and 314'. The marker 314 has a line which indicates the amount of carbohydrate which has been consumed. The open marker 314' indicates that carbohydrates have been consumed but it is unknown in which amounts.

The plot further has an insulin amount axis 316. The plot further has insulin discrete markers 318 and 318'. The insulin discrete marker 318 has a line which extends along the insulin amount axis 316 indicates the amount of insulin injected or received. The hollow marker 318' indicates that insulin has been injected or received but it is unknown in which amounts. The plot further shows two heart-shaped event markers 320. These are positioned along the time axis 300 to indicate when events which affect the health or wellbeing of the subject have occurred. For example an event marker may indicate illness or symptoms, or even exercise.

At the lower portion of the graphical user interface 138 there are a number of shortcuts 322. Pressing one of these shortcuts 322 may enable a user to view and/or edit archived data.

Figure 4:
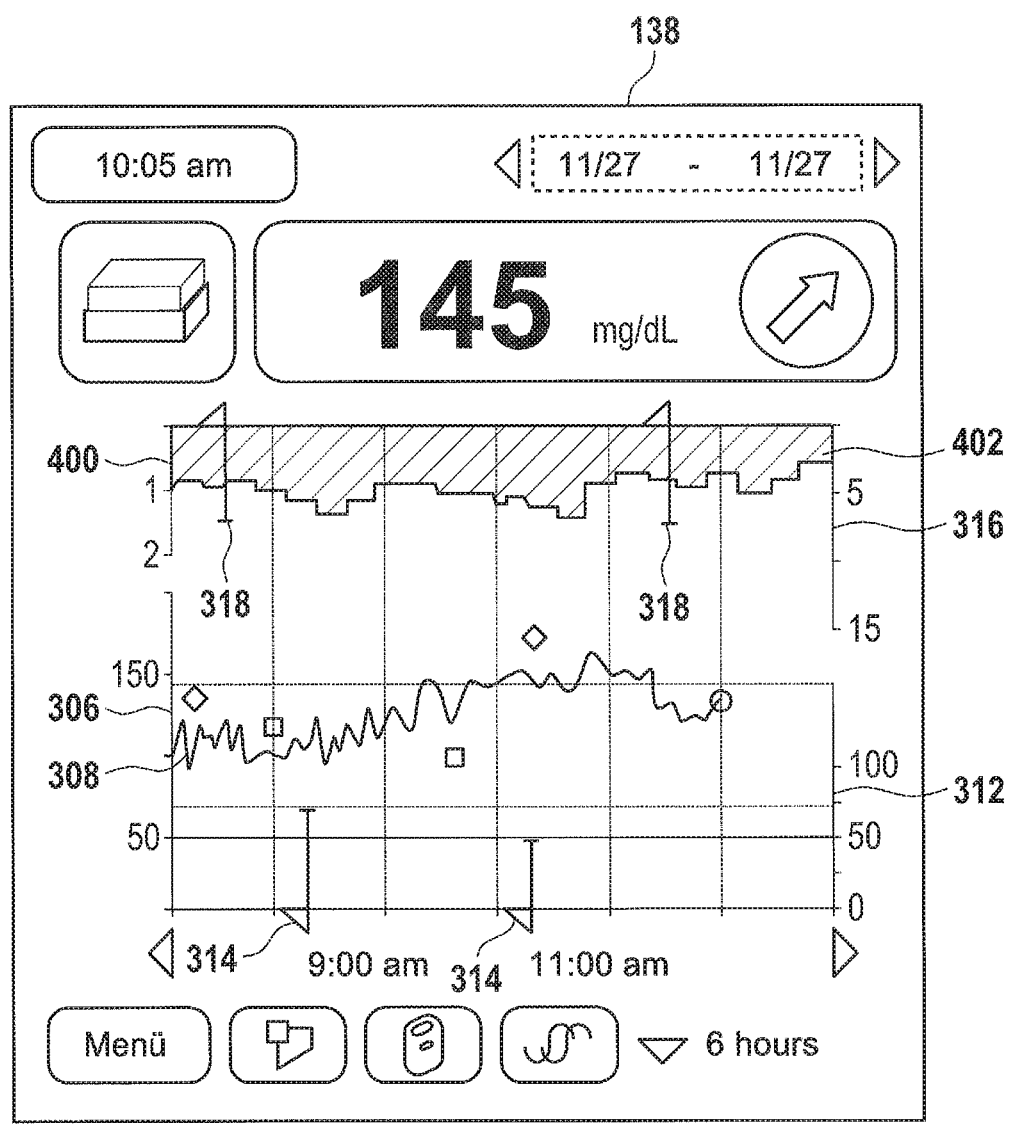
FIG. 4 illustrates an example of a graphical user interface.

FIG. 4 shows an alternative version of the graphical user interface 138. In this example the handheld device is also used in conjunction with an insulin pump. The plot further comprises a basal rate axis 400. In conjunction with this axis the plot of the basal rate 402 of an insulin pump is also shown.

Figure 5:
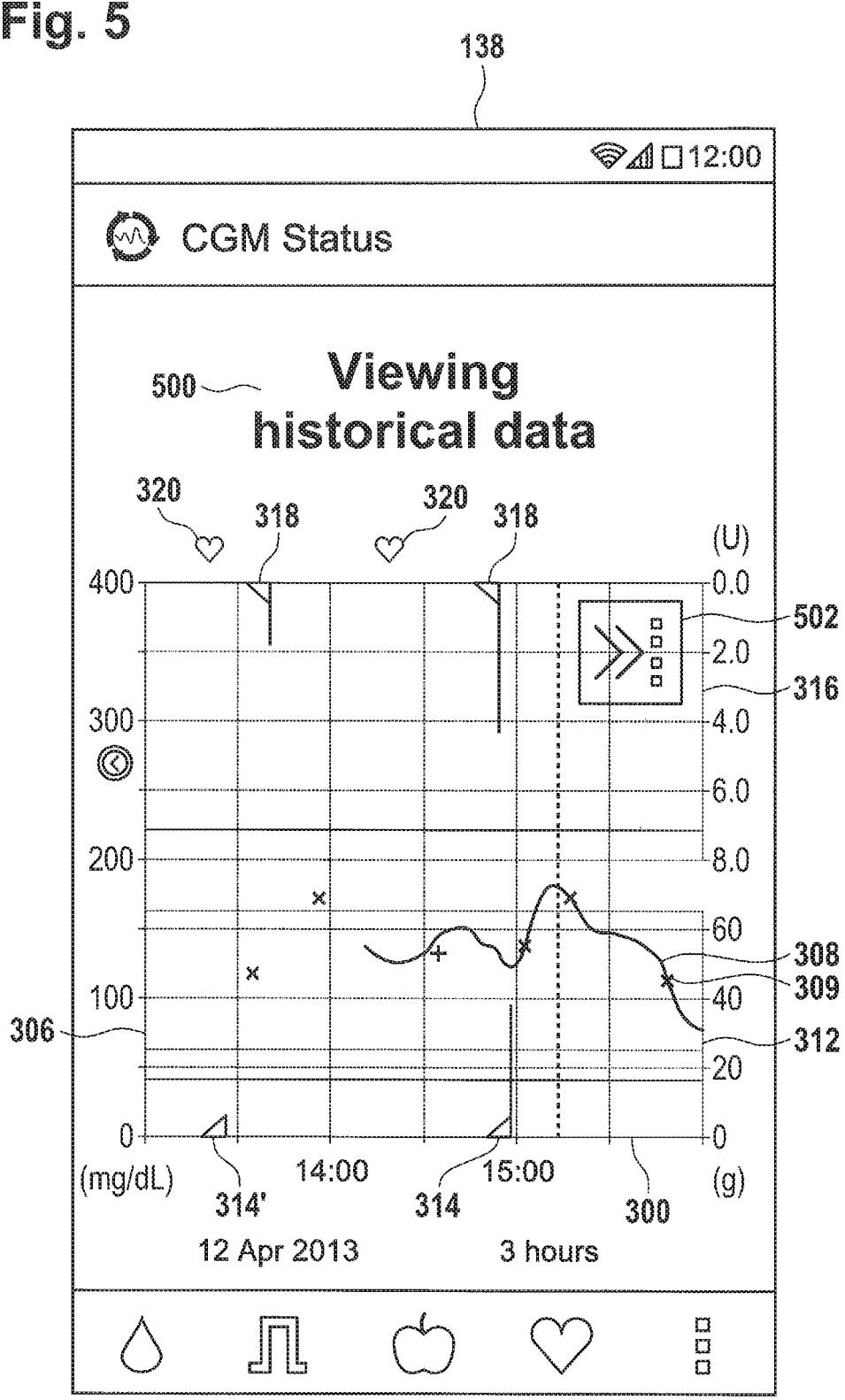
FIG. 5 illustrates an example of a graphical user interface.

FIG. 5 shows a further view of the user interface 138 as was illustrated in FIG. 3. In this example the user interface has been put into a historical data viewing mode. In this case the current sensor data value 302 and the trend arrow 304 are not displayed and instead a message 500 indicates that the data being viewed is historical. The user can then manipulate and look at the previously recorded data. There is a button 502 which when pressed allows the user of the handheld display device to return to the current data.

After pressing the button 502 the view returns to the view shown in FIG. 3. Additional data can also be displayed from this graphical user interface by touching the shortcuts 322 at the bottom of the graphical user interface 138.

Figure 6:
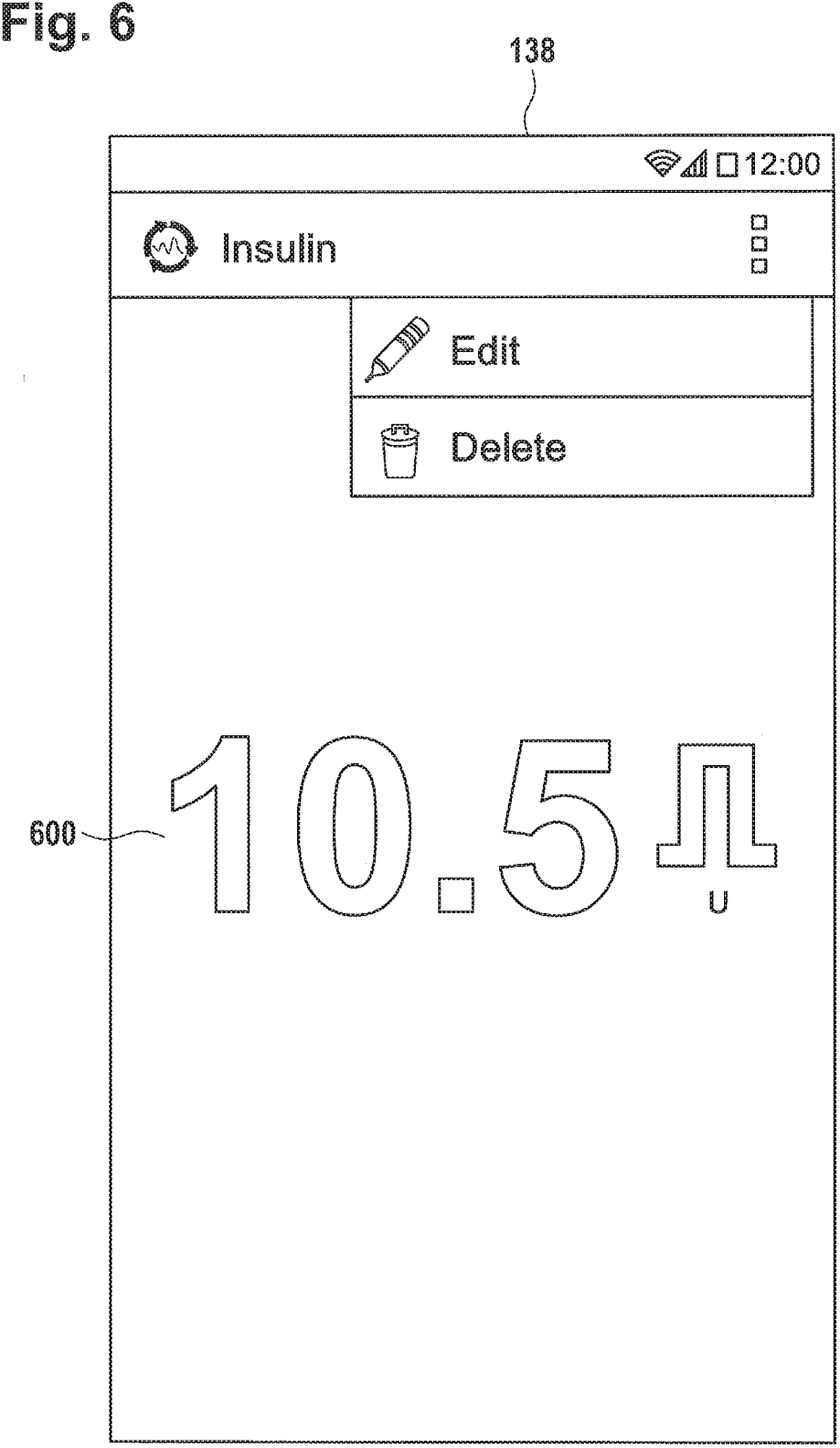
FIG. 6 illustrates an example of a graphical user interface.

FIG. 6 shows an example of the user interface 138. Such a user interface 138 may for example be displayed after a symbol for health events 320, carbs 314, or in this case insulin 319 is pressed. This shows a recorded value of 10.5. This user interface enables the operator of the handheld display device to see particular values and/or to edit or correct them. There may also be another interface or interfaces which enables the operator of the handheld display device to enter values for carbohydrates, blood glucose, and insulin or select from health events from a list.

Figure 7:
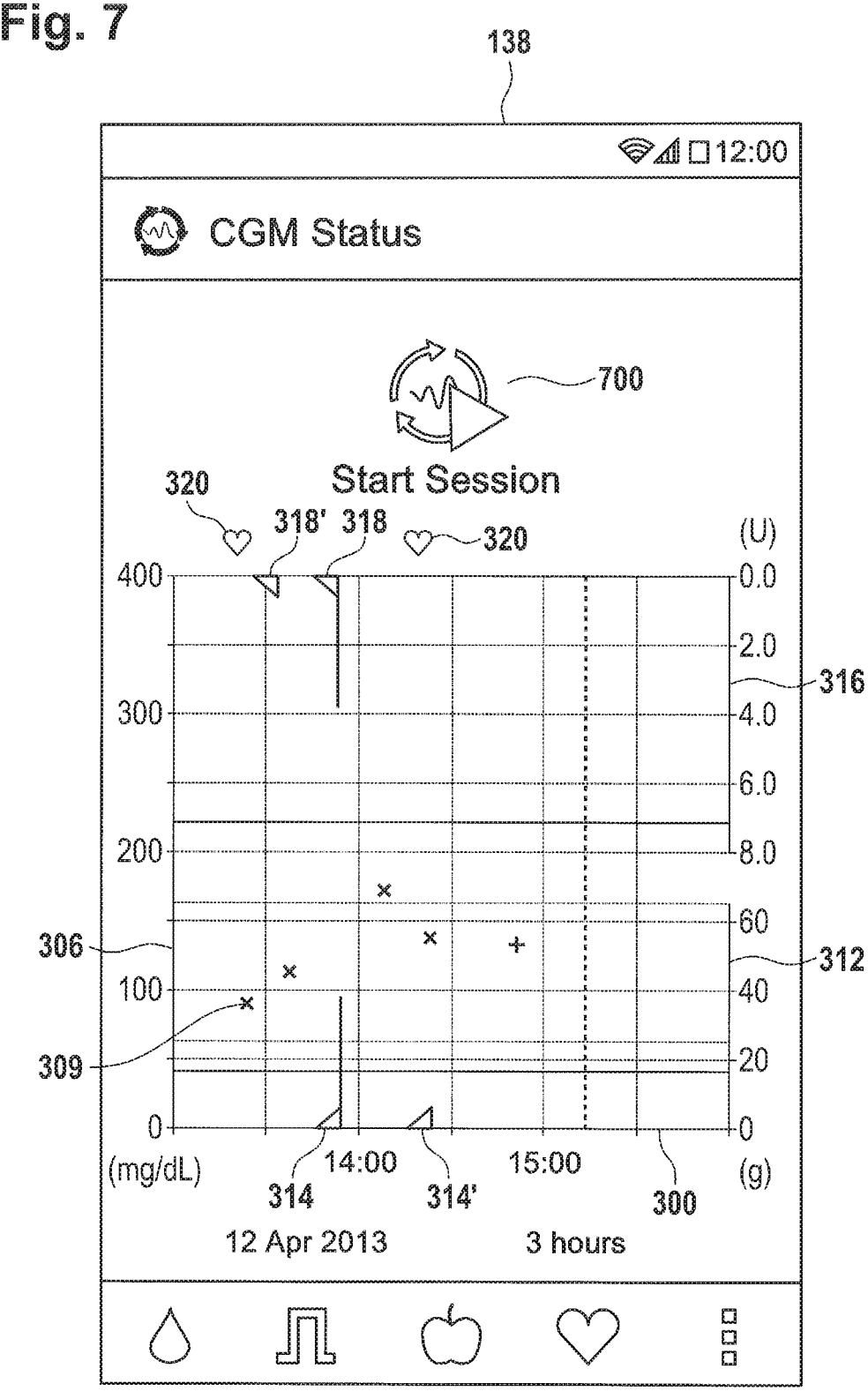
FIG. 7 illustrates an example of a graphical user interface.

FIG. 7 shows an alternate functioning mode of the handheld display device. The graphical user interface 138 is the same as is shown in FIG. 3 except the plot of the analyte concentration 308 is not shown. This illustrates that the handheld device can be used purely for data analysis in a way which is independent of that received from the body worn portion. This may be useful in a situation where the sensors are not functioning such as when the subject decides not to wear a sensor or when the sensor malfunctions and the subject needs to, for example, administer and determine blood glucose levels independent of a sensor and/or automatic insulin pump. This may be a useful tool which provides an additional safety factor in case all of the subject's equipment is not working properly.

FIGS. 8-13 are used to explain how a possible bolus model may be implemented within the handheld display device. The so called insulin action time as a result of a bolus may be personalized for an individual. In order to understand how the programmable feature allows users to individualize their blood glucose. it may be beneficial to understand the impact of the administered insulin on the bolus. This may be expressed by the insulin action time settings. The handheld display unit may utilize each user's individual settings through these parameters when calculating bolus recommendations.

The offset time is the length of time until significant blood glucose lowering begins. The offset time used or which may be used is an estimate of time it takes for the insulin bolus to begin significantly lowering the blood glucose. A reduction of blood glucose by 15 mg/dl or 0.83 mmol/L is considered significant. The offset time is essentially a combination of the insulin onset or the time it takes for the insulin to begin entering the bloodstream and the beginning of peak activity which is the time it takes to achieve maximum effect on lowering the blood glucose. As a safety feature the minimum setting for the offset time may be about 45 minutes.

Figure 8:
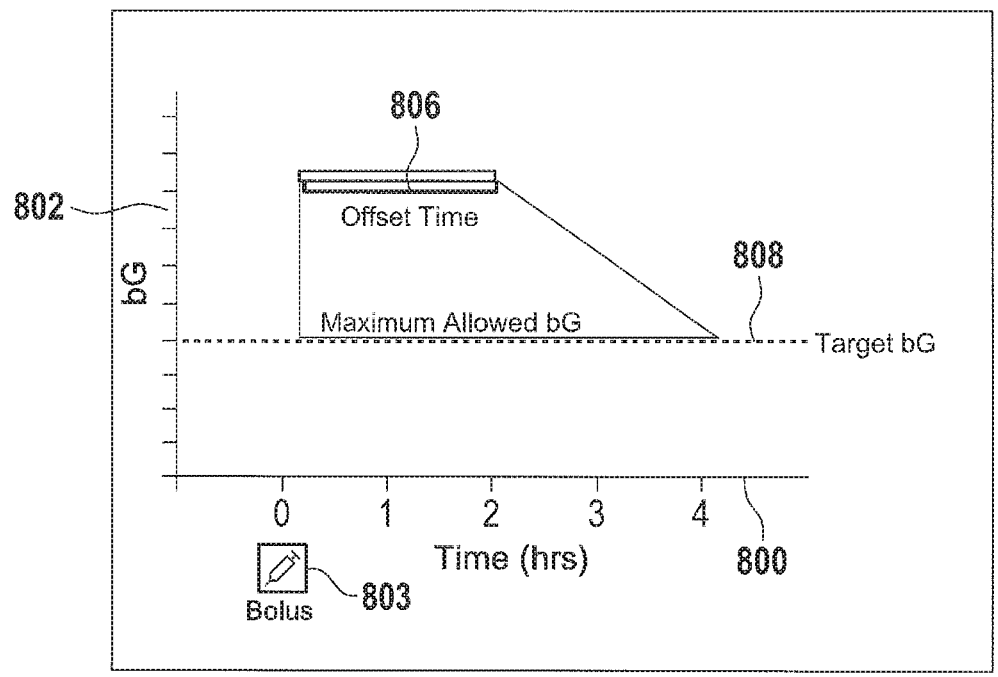
FIG. 8 shows a plot which is used to illustrate a method of personalizing a bolus model for the handheld display device of FIG. 1.

FIG. 8 illustrates these principles. The axis 800 is time. At time equals 0 is the bolus 803 is administered. The plot 802 illustrates the blood glucose. The target blood glucose is indicated by the dashed line 808 and the line 806 is the above described offset time.

The offset time is an important factor for calculating a correction dose because it affects how quickly the algorithm considers the blood glucose lowering potential of the administered insulin. A correction bolus may be for example recommended if the actual blood glucose remains at the initial level longer than anticipated.

Figure 9:
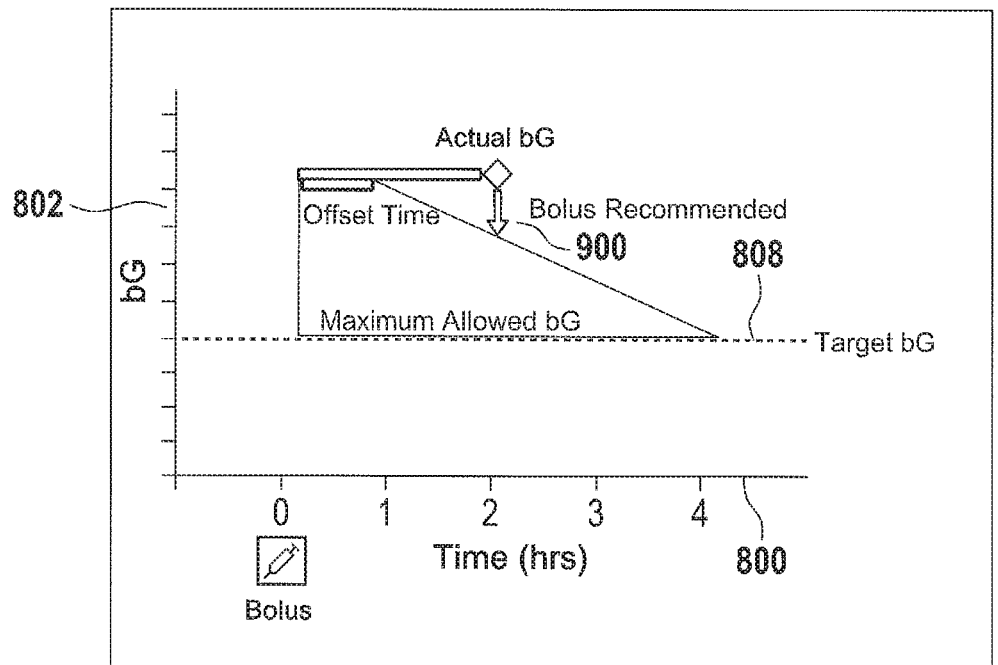
FIG. 9 shows a further plot which is used to illustrate a method of personalizing a bolus model for the handheld display device of FIG. 1.

FIG. 9 shows an example of when a shorter offset time is needed. A shorter offset time facilitates tighter control because the insulin is expected to begin lowering the blood glucose earlier than with a longer offset time. The arrow 900 indicates when a bolus is recommended.

Figure 10:
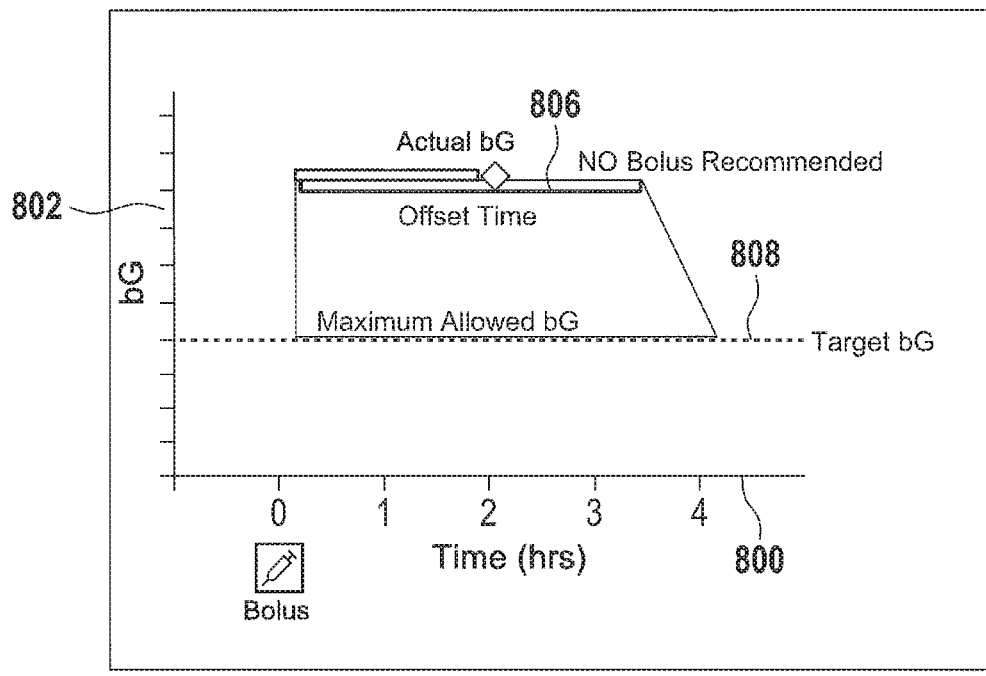
FIG. 10 shows a further plot which is used to illustrate a method of personalizing a bolus model for the handheld display device of FIG. 1.

FIG. 10 represents a longer offset time. A longer offset time will provide less aggressive blood glucose control because the algorithm will not expect an early decline in blood glucose. In this case it is not recommended to provide a correction bolus dose of insulin.

Another factor when personalizing bolus model is to consider the acting time. The acting time is the total length of time the insulin remains effective in lowering the blood glucose. The acting time is the total duration of time in that the bolus insulin is active in effectively lowering blood glucose based on each patient's individual physiology. The event database 168 can be analyzed by the learning algorithm to provide this information.

Figure 11:
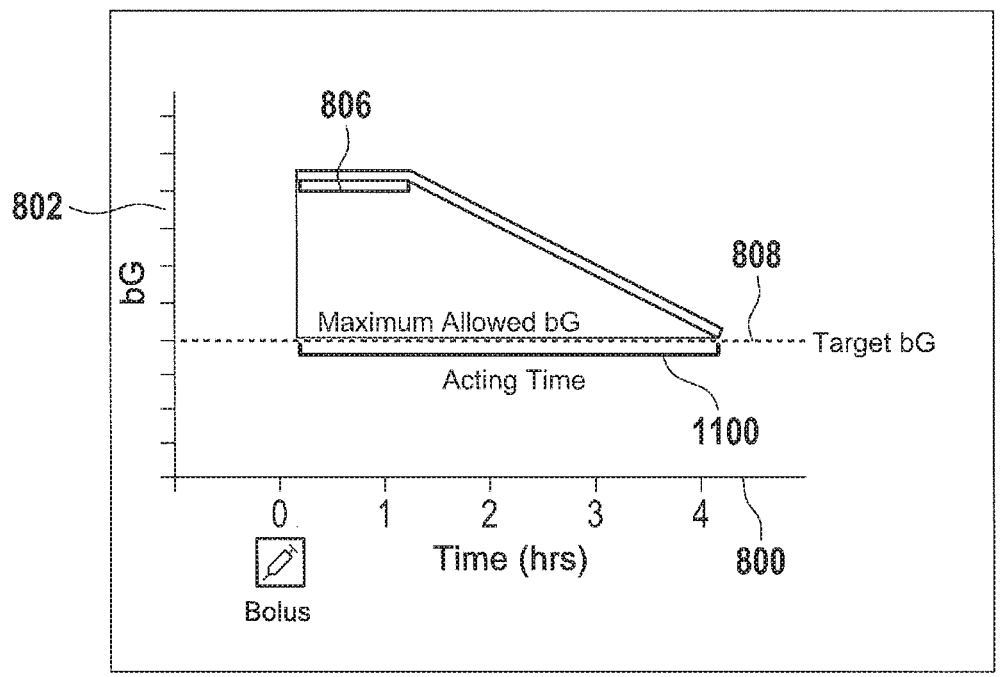
FIG. 11 shows a further plot which is used to illustrate a method of personalizing a bolus model for the handheld display device of FIG. 1.

FIG. 11 is similar to FIG. 8 except in this case the acting time 1100 is indicated.

The acting time is affected by the insulin type used and the average bolus size. Insulin analogues have a shorter acting time than regular insulin. Large boluses tend to delay insulin action and prolong the acting time. It may be beneficial to seek an accurate acting time in order to safely achieve good blood glucose control. In this case the data storage and analysis capabilities of the handheld display device may be useful in determining the acting time accurately for different types of insulin and doses for a particular individual or subject.

Figure 12:
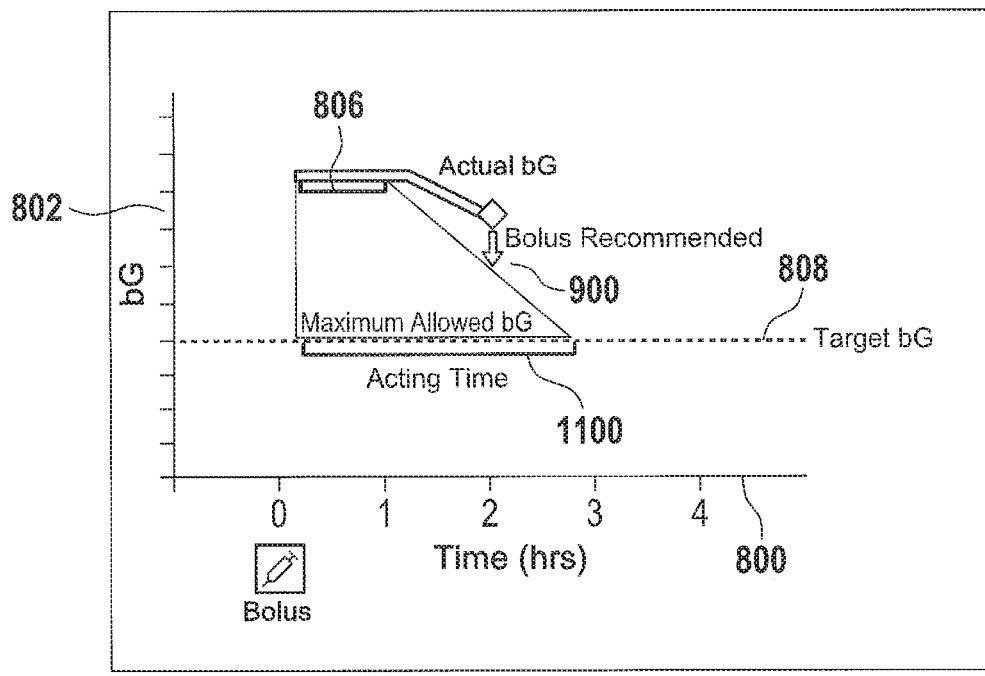
FIG. 12 shows a further plot which is used to illustrate a method of personalizing a bolus model for the handheld display device of FIG. 1.

FIG. 12 shows the effect if the acting time is too short. If the acting time is too short there is potential danger for insulin stacking because the bolus advisor does not recognize any available active insulin. In FIG. 12 it can be seen that the actual blood glucose is decreasing less rapidly than is anticipated.

Figure 13:
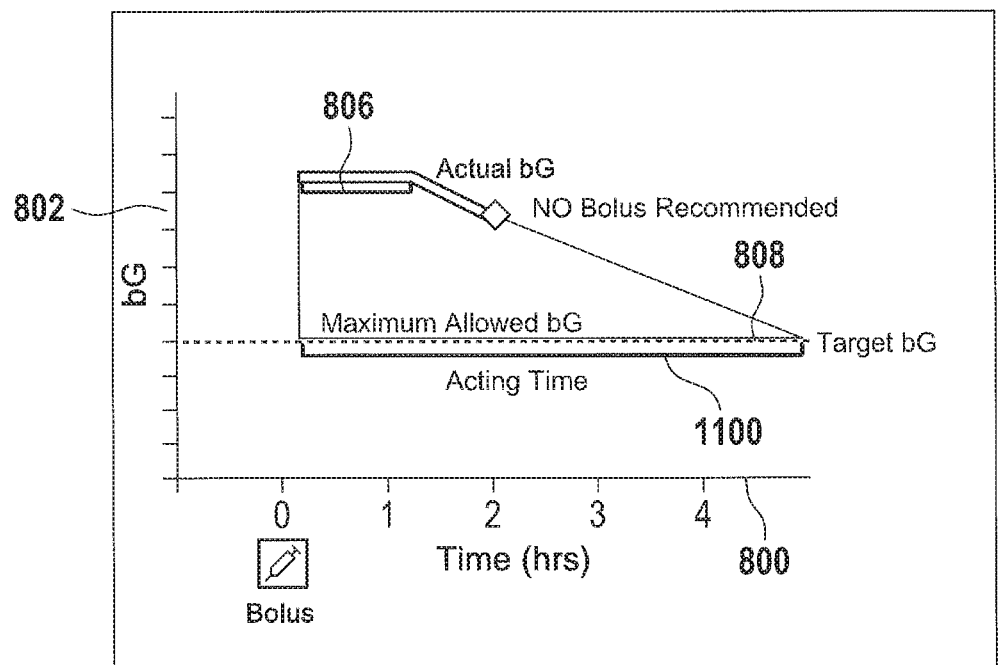
FIG. 13 shows a further plot which is used to illustrate a method of personalizing a bolus model for the handheld display device of FIG. 1.

FIG. 13 shows the effect of setting the acting time too long. The bolus advisor recognizes an exaggerated amount of available active insulin which may lead to under-dosing in correction boluses.

By analyzing the events in the database, it may be possible to accurately determine the insulin sensitivity of a subject. For the current time block, the insulin sensitivity or correction factor is the amount of insulin necessary to lower the blood glucose by a certain amount. This may be useful for more accurate bolus recommendations. The carb or carbohydrate ratio is the amount of insulin necessary to account for a certain number of carbohydrates. This can also be determined from the event database by accurately monitoring the effects of insulin in relation to the actual number of calories of carbohydrate consumed by the subject.

FIG. 14 illustrates an example of a one finger gesture using the display with the graphical user interface 138 of FIG. 3. In FIGS. 14 and 15, the display with the graphical user interface is implemented using a gesture recognition component. The gesture recognition component may for example be a touch screen.

In FIG. 14, a view 1400 of the display 138 before the finger gesture is performed and a view after 1402 the finger gesture is performed is shown. The finger gesture is represented by the arrow 1404. A single finger 1406 is moved across the display 138 in the direction of the arrow 1404. In this example the single finger gesture 1404 is used to shift a concentration range 306. To perform this gesture, a user places one finger 1406 on the displayed graph 308. The finger is then slid upwards (following the arrow 1404) or downwards (going opposite to the arrow 1404). The position of the graph will shift in the same direction. Sliding upwards shifts the concentration range 306 to smaller values. Siding downwards shifts the concentration range 306 to larger values. In some examples moving the finger side to side will shift the time axis in a similar manner.

The example of the finger gesture illustrated in FIG. 14 is useful for shifting the concentration range 306. The single finger gesture 1404 can be used to move the graph 308 upwards or downwards to make a different concentration range 306 visible. If, for example the trend curve 308 is no longer or only partially visible (such as is the case in view 1400 FIG. 14), an operator can pull the trend curve 308 back into the visible area on the display 138 (as is shown in view 1402 in FIG. 14).

FIG. 15 illustrates an example of a two finger gesture using the display with the graphical user interface 138 of FIG. 3. The two finger gesture of FIG. 15 may also be referred to as a "pinch gesture." Similar to FIG. 14, a view 1500 of the display 138 before the finger gesture is performed and a view 1502 after the finger gesture is performed is shown. The double finger gesture is represented by the arrow 1504. Two fingers 1506 are placed on the display 138 and are either moved apart in the direction indicated by the arrow 1504 or are moved together in a pinching movement in opposition to the direction indicated by the arrow 1504.

In the example of FIG. 15, the double finger gesture 1504 is used to change the scale of the concentration range 306. To perform this gesture, a user places two fingers 1506 on the displayed graph 308 and either slides them apart or slides them together in a pinching movement. The further apart the fingers 1506 are slid, the larger the graph magnification. To reduce the magnification of the axis 306, the fingers 1506 are slid towards each other in a pinching movement. In some examples moving the fingers 1506 together or apart in a direction perpendicular to the arrow 1504 can be used to reduce or enlarge the time scale 300.

In FIG. 15, the two finger gesture 1504 can be used to magnify or reduce the visible concentration range 306. The value axes 316 and 312 remain unchanged in this example. It can be seen that in view 1502 the scale of the concentration range 306 has been magnified or increased, but the curve 308 is partially outside of the displayed concentration range. View 1502 of FIG. 15 shows the same user interface 138 as view 1400 of FIG. 14. After performing the two finger gesture 1504, the user may perform gesture 1404 (as is illustrated by FIG. 14) to shift the concentration range 306 so that the complete curve 308 is visible.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMERALS 100 medical system
102 handheld display device
104 body worn portion
106 skin
108 subcutaneous region
110 subcutaneous portion (sensor)
112 medical module (monitoring system)
114 first processor
116 first wireless communication module
118 first memory
120 first battery
122 body worn portion instructions
124 sensor data (analyte concentration)
130 second battery
132 second wireless communication module
134 second processor
136 second memory
138 display with graphical user interface
140 data exchange interface
142 wireless communication channel
150 operating system
154 carbohydrate data
156 insulin data
158 event data
160 sensor data scaling factor
162 carbohydrate data scaling factor
164 insulin data scaling factor
166 executable instructions
168 event database
170 learning algorithm instructions
172 bolus model instructions
200 receive the sensor data via the communication channel continuously
202 receive carbohydrate data via the graphical user interface or via a carbohydrate data transfer interface
204 receive event data via the graphical user interface or via an event data transfer interface
206 receive insulin data via the graphical user interface or via an insulin data transfer interface
208 determine a sensor data scaling factor, a carbohydrate data scaling factor and an insulin data scaling factor
210 control the graphical user interface to render a plot on the graphical user interface
300 time axis
302 current sensor data value
304 trend arrow
306 analyte concentration axis
308 plot of analyte concentration
309 blood measurement
310 current time cursor
312 carbohydrate amount axis
314 carbohydrate discrete marker
314' carbohydrate discrete marker
316 insulin amount axis
318 insulin discrete marker
318' insulin discrete marker
320 event marker
322 shortcuts
400 basal rate axis
402 plot of basal rate
500 message
502 button
600 recorded value
800 time
802 blood glucose
803 bolus event
804 maximum allowed bolus
806 offset time
808 target bolus
900 recommended bolus
1100 acting time
1400 graphical user interface before gesture
1402 graphical user interface after gesture
1404 one finger gesture
1408 singe finger
1500 graphical user interface before gesture
1502 graphical user interface after gesture
1504 two finger gesture
1506 two fingers

What is claimed is:

1. A handheld display device for processing sensor data continuously measured by an implantable analyte sensor, comprising:
 a communication interface configured to receive sensor data from the analyte sensor via a wired or wireless communication channel;
 a graphical user interface having a gesture recognition component, wherein the graphical user interface is configured for receiving double finger gestures;
 a processor and a memory, the processor configured to:
 (a) continuously receive the sensor data via the communication interface, wherein the sensor data is indicative of an analyte concentration in bodily fluid and is time dependent;
 (b) receive time dependent carbohydrate data via the graphical user interface or via a carbohydrate data transfer interface, wherein the carbohydrate data is indicative of carbohydrate intake by the subject;
 (c) receive time dependent event data via the graphical user interface or via an event data transfer interface, wherein the event data is indicative of a physical state of the subject;
 (d) receive time dependent insulin data via the graphical user interface or via an insulin data transfer interface, wherein the insulin data is indicative of an insulin delivery to the subject;
 (e) determine a sensor data scaling factor, a carbohydrate data scaling factor and an insulin data scaling factor, wherein the scaling factors are based on an adjustable display time frame and the corresponding data received in the adjustable display time frame;
 (f) render a plot on the graphical user interface, the plot having a single time axis, an analyte concentration axis, a carbohydrate amount axis, and an insulin delivery amount axis, wherein:
  i. the analyte concentration axis is rendered on a first side of the plot according to the sensor data scaling factor,
  ii. the insulin delivery amount axis and the carbohydrate amount axis are rendered on a second side opposite to the first side of the plot according to the carbohydrate data scaling factor and the insulin data scaling factor, respectively,
  iii. the sensor data is rendered continually,
  iv. the carbohydrate data is rendered continually and/or as a carbohydrate discrete marker, and
  v. the insulin data is rendered continually and/or as an insulin discrete marker;

(g) receive the double finger motion from the gesture recognition component, wherein the double finger gestures comprise a double finger motion parallel to a selected axis selected from the analyte concentration axis, the carbohydrate amount axis, and the insulin delivery amount axis, wherein the double finger motion is descriptive of an increase or decrease of distance between two fingers measured along the selected axis;

(h) control the graphical user interface to magnify or shrink only the selected axis using the increase or decrease of the distance between the two fingers measured along the selected axis;

(i) receive the single finger motion from the gesture recognition component; and (j) control the graphical user interface to shift the selected axis using the single finger motion.

2. A medical system comprising:
the handheld display device of claim 1; and
a body worn portion configured for attaching to an outer surface of a subject, wherein the body worn portion further comprises the analyte sensor, and wherein the body worn portion is configured for exchanging data with the handheld display device via the communication channel.

3. The medical system of claim 2, wherein the analyte concentration is a glucose concentration, and wherein the sensor is a subcutaneous glucose sensor.

4. The handheld display device of claim 1, wherein the processor is further configured to calculate a suggested bolus using at least one of a bolus model, the sensor data, the carbohydrate data, the insulin data, and the event data, wherein the plot further comprises a bolus indicator that displays an injection time and an injection amount, wherein the injection time is displayed on the time axis and the injection amount is displayed as a length perpendicular to the time axis.

5. The handheld display device of claim 4, wherein the suggested bolus is a discrete amount of insulin to be delivered in order to adjust the blood glucose level to within a predetermined or customized range.

6. The handheld display device of claim 5, wherein the discrete amount of insulin is configured to be delivered to adjust the blood glucose level before or after a meal.

7. The handheld display device of claim 4, wherein the suggested bolus is displayed in response to received carbohydrate data.

8. The handheld display device of claim 1, further comprising an event database configured for logging any one of the following: the sensor data, the carbohydrate data, the event data, the insulin data, and combinations thereof.

9. The handheld display device of claim 8, further comprising a learning algorithm module configured for correcting the bolus model using the event database.

10. The handheld display device of claim 1, further comprising an insulin pump for injecting insulin into the subject, wherein the plot further comprises a time dependent display of the basal rate.

11. The handheld display device of claim 1, wherein the processor is further configured to display a trend arrow whose direction is dependent upon a current sensor data derivative value determined from the sensor data.

12. The handheld display device of claim 1, wherein the processor is further configured to display a current analyte concentration value determined from the sensor data.

13. The handheld display device of claim 1, wherein the graphical user interface is configured for receiving a single finger motion parallel to a selected axis selected from the analyte concentration axis, the carbohydrate amount axis, and the insulin delivery amount axis, wherein the processor is configured to shift the selected axis using the single finger motion.

14. A method of operating a handheld display device for processing sensor data continuously measured by an implantable analyte sensor having a communication interface configured to receive sensor data from the analyte sensor via a wired or wireless communication channel, a graphical user interface that has a gesture recognition component configured for receiving double finger gestures, the method comprising the following steps:

(a) continuously receiving the sensor data via the communication interface, wherein the sensor data is indicative of an analyte concentration in bodily fluid and is time dependent;

(b) receiving time dependent carbohydrate data via the graphical user interface or via a carbohydrate data transfer interface, wherein the carbohydrate data is indicative of carbohydrate intake by the subject;

(c) receiving time dependent event data via the graphical user interface or via an event data transfer interface, wherein the event data is indicative of a physical state of the subject;

(d) receiving time dependent insulin data via the graphical user interface or via an insulin data transfer interface, wherein the insulin data is indicative of an insulin delivery to the subject;

(e) determining a sensor data scaling factor, a carbohydrate data scaling factor and an insulin data scaling factor, wherein the scaling factors are based on an adjustable display time frame and the corresponding data received in the adjustable display time frame;

(f) rendering a plot on the graphical user interface comprising a single time axis, an analyte concentration axis, a carbohydrate amount axis, and an insulin delivery amount axis, wherein:
  i. the analyte concentration axis is rendered on a first side of the plot according to the sensor data scaling factor,
  ii. the insulin delivery amount axis and the carbohydrate amount axis are rendered on a second side opposite to the first side of the plot according to the carbohydrate data scaling factor and the insulin data scaling factor, respectively,
  iii. the sensor data is rendered continually,
  iv. the carbohydrate data is rendered continually and/or as a carbohydrate discrete marker, and
  v. the insulin data is rendered continually and/or as an insulin discrete marker;

(g) receiving the double finger motion from the gesture recognition component, wherein the double finger gestures comprise a double finger motion parallel to a selected axis selected from the analyte concentration axis, the carbohydrate amount axis, and the insulin delivery amount axis, wherein the double finger motion is descriptive of an increase or decrease of distance between two fingers measured along the selected axis;

(h) controlling the graphical user interface to magnify or shrink only the selected axis using the increase or decrease of the distance between the two fingers measured along the selected axis;

(i) receiving the single finger motion from the gesture recognition component; and (j) controlling the graphical user interface to shift the selected axis using the single finger motion.

15. The method of claim 14, wherein the graphical user interface is configured for receiving single finger gestures comprising a single finger motion parallel to a selected axis selected from the analyte concentration axis, the carbohydrate amount axis, and the insulin delivery amount axis, the method further comprising:

receiving the single finger motion from the gesture recognition component; and controlling the graphical user interface to shift the selected axis using the single finger motion.

* * * * *